United States Patent [19]

Faber et al.

[11] 4,342,831

[45] Aug. 3, 1982

[54] FERMENTABLE ACID HYDROLYZATES AND FERMENTATION PROCESS

[75] Inventors: Marcel D. Faber, Princeton; Richard H. Ernst, Kendall Park; Philip H. Lefebvre, Spotswood, all of N.J.

[73] Assignee: American Can Company, Greenwich, Conn.

[21] Appl. No.: 252,351

[22] Filed: Apr. 9, 1981

Related U.S. Application Data

[63] Continuation of Ser. No. 53,979, Jul. 2, 1979, abandoned.

[51] Int. Cl.³ .............................................. C12P 7/06
[52] U.S. Cl. .................................. 435/163; 435/161; 127/37
[58] Field of Search .................. 435/161, 163; 127/37

[56] References Cited

U.S. PATENT DOCUMENTS

2,203,360  6/1940  Partansky .............................. 127/37
3,212,933 10/1965  Hess et al. ............................. 127/37

*Primary Examiner*—Alvin E. Tanenholtz
*Attorney, Agent, or Firm*—Ernestine C. Bartlett

[57] ABSTRACT

Method of preconditioning acid hydrolyzates derived from lignocellulosic materials such as sawdust or newspaper and preconditioned acid hydrolyzates are provided. The preconditioning negates the effect of substances which tend to inhibit fermentation and comprises a series of steps including steam-stripping, calcium oxide treatment at a pH of 10 to 10.5, adjusting the pH to about 6 to 7 with a mineral acid and especially phosphoric acid and concentrating the hydrolyzate solution to a glucose concentration of less than 150 grams per liter. Glucose contained in such preconditioned hydrolyzates is readily fermentable to ethyl alcohol, in theoretical yield, after fermentation for as short a period as 1 to 2 hours.

27 Claims, No Drawings

FERMENTABLE ACID HYDROLYZATES AND FERMENTATION PROCESS

This is a continuation application of application Ser. No. 053,979 filed July 2, 1979 and now abandoned.

BACKGROUND OF THE INVENTION

Traditionally, used wood, paper and agricultural byproducts, such as sawdust, woodwaste, corncobs, straw, sugar cane bagasse, newspaper and the like have been regarded essentially as waste materials, and have been disposed of through incineration or by other, similarly unproductive, means. It is well known that the lignocellulosic constituents of such materials can be hydrolyzed to produce more valuable products which in turn can be converted into additional and different valuable products; however, such operations are in limited use, due largely to the relatively low returns on investment which they have been capable of generating. The capital expenditures required to design and construct the facilities for carrying out such recovery operations tend to be significant, thus demanding that relatively high conversion rates be attainable in order to justify the expense involved.

In U.S. Application Ser. No. 2,885 filed Jan. 12, 1979 now, U.S. Pat. No. 4,201,596 issued May 6, 1980 of John A. Church et al entitled "Continuous Process For Cellulose Saccharification" and commonly assigned herewith, there is described a method and apparatus for saccharification of cellulosic products in which the cellulosic constituents of typical waste products may be converted into glucose, furfural and xylose. Such a process conveniently, rapidly and economically provides by acid cellulose hydrolysis, a hydrolyzate which may be used as the raw material for the production of more valuable products. For example, as disclosed in said U.S. Pat. No. 4,201,596 such hydrolyzates may be used as the raw fermentable substance in a process for converting sugar into ethyl alcohol.

While it has long been known that cellulosic hydrolyzate solutions may be made fermentable for the production of alcohols, prior procedures have been feasible only on a small laboratory scale and have not significantly developed beyond this stage. Among the principal conditions contributing to this state of the art has been the inordinately slow rates of reaction with extremely low yield and the lack of predictability of conditions that would permit fermentation with any given hydrolyzate. Additionally, the economic considerations inherent in the chemical conversion of sugar to alcohol have been a limiting factor. For example, it is only theoretically possible to obtain one unit of alcohol from every two units of sugar present in the raw material. Losses in sugar content of the raw material through process conditions, mechanical processing, etc., serve to even further decrease the low yields that it has been possible to obtain.

Cellulosic extractives and their decomposition products as fermentable raw materials have been particularly enigmatic to approach because of the wide variety of factors, many of which are unknown, that adversely affect and, in many cases, prevent the fermentation process. One factor that has long been recognized in the art as significantly retarding the development of a feasible fermentation process has been the presence of materials in the hydrolyzate that act as toxins or fermentation inhibitors. However, the toxins present in any given hydrolyzate may vary considerably depending on its processing history, its source, etc. Moreover, the problem is further compounded by the fact that even after the particular toxins have been identified in a given hydrolyzate, their action under any given set of conditions has been largely unpredictable and fermentation has been difficult even under special conditions. Various workers in the art have suggested that these difficulties may be dependent on any number of factors including processing temperatures, pH of the media, the presence or absence of oxygen, the concentration and type of toxin substance, the ratio of yeast cells to toxin substances, the physiological condition of the yeast cells, the wide variation in the toxicity of various substances on the metabolism of the particular yeast, the oxidation-reduction potential developed during reaction, and many other factors. Discussions of the various difficulties of fermentation and general factors influencing fermentation are found in many sources in the literature.

Cumulative discussions are given by Harris et al in "Fermentation of Douglas Fir Hydrolyzates by *S. cerevisiae*" and Leonard et al, "Fermentation of Wood Sugars to Ethyl Aclohol;" *Industrial and Engineering Chemistry*, Vol. 38, pp. 896 to 904, (1946) and Vol. 37, pp. 390 to 397, (1946), respectively.

Other workers in the art include Eklund et al, "Acid Hydrolysis of Sunflower Seed Husks for Production of Single Cell Protein," *European Journal of Applied Microbiology*, Vol. 2, pp. 143–152 (1976) who disclose a method of hydrolyzing sunflower seed husks and degradation of the resulting hydrolyzate to produce protein.

German Pat. No. 676,967 to Scholler (1939) describes a method for clarifying xylose worts obtained by acid hydrolysis of cellulose-containing substances for feed purposes or yeast production by precipitating calcium phosphate and calcium sulfate after heating to 65° to 100° together with centrifuging and conducting the wort over oxidized metal fillings or large surface area materials while the wort is at a pH of 4 to 7.5, adding malt sprouts to the thus clarified wort and stirring for several hours.

U.S. Pat. No. 2,203,360 dated June 4, 1940 to Partansky discloses a method for improving the fermentation characteristics of acid wood hydrolyzates by treating the hydrolyzate with lime to adjust the pH to between 9 and 10, aging for 1 to 2 days, reducing the pH with sulfuric acid to pH 5, purifying the solution with activated charcoal, diluting the solution to contain 40–70% by volume of hydrolyzate, inoculating the solution with yeast culture and fermenting for 2 days.

The prior art, as represented by the methods discussed above, is illustrative of the absence of a feasible commercial process for fermentation of acid hydrolyzates to alcohols due to inordinately slow reaction times and low yields and/or the lack of direction for obtaining the same. A method for readily and efficiently producing alcohol by fermentation of sugars present in wood and wood-byproducts is a particularly timely and significant development in view of current interest in alcohol as a potential energy source available from renewable raw materials.

A primary object of this invention is to provide a process for fermentation of sugars present in acid hydrolyzates derived from lignocellulosic materials.

Another object of the invention is to provide such a process in which reaction times are relatively short, in which fermentation may be effected at relatively high sugar concentrations and in which control mechanisms are established which permit predictability, reproduction of results with consistency and production of end products of high value.

Another object of this invention is to provide a process in which the acid hydrolyzate of cellulosic waste materials may be converted into ethyl alcohol.

The accomplishment of these and other objects will be apparent from the description of the invention which follows:

SUMMARY OF THE INVENTION

The foregoing and related objects of this invention are attained in a method for preconditioning acid hydrolyzates, derived from lignocellulosic materials, to negate the effect of substances tending to inhibit the fermentation of such hydrolyzates and to a process for the production of ethyl alcohol from glucose contained in such preconditioned acid hydrolyzates. The hydrolyzate is preconditioned to remove and/or reduce or otherwise negate the effect of inhibitory substances to a level whereby the hydrolyzate may be readily fermented to ethyl alcohol in substantially theoretical yield.

The preconditioning method broadly comprises the steps of:

(1) subjecting the hydrolyzate to steam to remove furfural and other steam-volatile substances therefrom;

(2) adding sufficient calcium oxide to the steam-stripped hydrolyzate, at room temperature, to adjust the pH to between about 10 and 10.5, maintaining the resulting mixture at said pH for about 1 to 3 hours and separating the hydrolyzate from the resultant precipitate;

(3) adding sufficient amounts of a mineral acid to adjust the pH of said hydrolyzate to about 5 to 7; and (4) adjusting the concentration of said hydrolyzate to a glucose concentration of less than about 150 grams per liter to provide a solution fermentable to ethyl alcohol.

The fermentation process broadly comprises the steps of:

(1) preconditioning an acid hydrolyzate to negate the effect of substances tending to inhibit the fermentation thereof by subjecting the hydrolyzate to the preconditioning method described hereinabove;

(2) inoculating the preconditioned hydrolyzate with yeast inoculum comprising from about 0.7 to about 7 dry weight percent of yeast cells per 100 grams per liter of glucose in the hydrolyzate;

(3) fermenting the inoculated hydrolyzate at a pH of 5 to 7 for a period sufficient to convert glucose to ethyl alcohol; and (4) recovering ethyl alcohol from the fermentation mixture.

In a preferred embodiment, yeast cells are recovered, reconcentrated and recycled to a subsequent fermentation medium comprising preconditioned, concentrated hydrolyzate.

General Disclosure

The process of this invention utilizes a combination of steps and conditions which are interrelated and interdependent for the successful achievement of the objectives of the invention. This interrelationship will best be seen from the following description of the effect or function of each particular sequence within the context of the total process.

Hydrolyzate Raw Material

The invention may be successfully realized with any hydrolyzate derived from the acid hydrolysis of lignocellulosic material. Such lignocellulosic material may be selected from a wide variety of materials including wood and paper and particularly used paper and wood by-products such as sawdust, wood waste, straw, sugar cane bagasse, rice hulls, newspaper and the like. Such materials may be hydrolyzed in the presence of an acid catalyst by methods well known in the art to provide a suitable hydrolyzate raw material for use in the process.

The hydrolyzate raw material provided will vary in sugar content and other components depending on the conditions under which it has been produced. This can be best understood by a consideration of the chemistry involved in acid hydrolysis stated for the sake of illustration in simplified terms. When cellulosic material is heated with dilute aqueous acid, glycosidic bonds which connect individual anhydroglucose units to one another in the cellulose molecule are cleaved by acid catalysis and one molecule of water adds to each anhydroglucose unit to form one molecule of glucose as illustrated by the idealized equation:

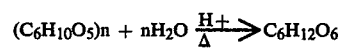

Glucose is inherently unstable in hot acid solutions and can lose three molecules of water to yield 5-hydroxymethyl furfural (HMF) according to the equation:

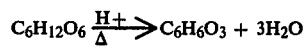

HMF in turn is unstable and can add two molecules of water to yield levulinic acid and formic acid:

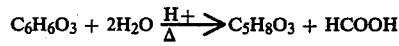

Other very complex reactions also occur in which it is believed HMF condenses into dark insoluble residues known as humins. Lignin breakdown products such as vanillin or other aromatic compounds may also be present. Additionally, the bonds of the hemicellulose molecule are cleaved to produce free molecules of xylose from xylan. Certain reaction conditions will favor formation of glucose or xylose and accompanying decomposition products.

An especially preferred method and apparatus for producing suitable acid hydrolyzate raw materials for use in this invention is that disclosed and claimed in said application Ser. No. 2,885 filed Jan. 12, 1979 now, U.S. Pat. No. 4,201,596 issued May 6, 1980 entitled "Continuous Process for Cellulose Saccharification" referred to hereinabove. As disclosed therein, whereas the xylan conversion to xylose occurs at relatively low temperatures, the cellulose conversion to glucose best occurs under more severe conditions. It has not been possible to produce maximum amounts of both xylose and glucose in a one phase method due to the fact that the xylose dehydrates to furfural under the conditions which most efficiently effect the conversion of cellulose to glucose. The method of said U.S. Pat. No. 4,201,596 defines the conditions which favor production of glucose/furfural and which minimize degradation of glucose to HMF and levulinic acid. Since, as discussed and illustrated further hereinbelow, furfural, HMF and levulinic acid are each toxins to the fermentation organism, the present invention most preferably utilizes a hydrolyzate raw material obtained under such conditions that minimize, to the extent possible, the presence of such toxin substances.

Such conditions in general provide for acid hydrolysis, in the presence of steam, of cellulose feedstock having a solids content of from about 20 to 45 weight percent at temperatures within the range of about 190° to 225° C. and pressures of about 200 to 400 psi with residence times in a reaction zone of about 1 to 10 minutes. In the reaction mass, the optimum amount of water after steam injection is about 75 to 80 weight percent and virtually any strong mineral acid can be employed to catalyze the hydrolysis reactant, sulfuric acid being normally the acid employed in amounts of about 1 to 3 percent based on the total weight of the reaction mass. In this preferred process for production of hydrolyzate raw material, the reaction mass will be subjected to an abrupt pressure reduction whereby a fraction of the hydrolyzate vaporizes and may be recovered. This fraction will normally comprise furfural and acetic acid.

It will be understood that the above description is for purposes of illustration of the preferred mode of obtaining an acid hydrolyzate that is especially suitable for use in the present invention. The method of the invention may utilize acid hydrolyzates from any source since it is a feature of the invention that the preconditioning method will serve to reduce or remove certain of the toxin materials to tolerable levels and/or to otherwise negate the effect of such materials without substantially adversely affecting the glucose present in the hydrolyzate.

Such hydrolyzate raw materials will in general, however, comprise glucose, furfural, 5-hydroxymethylfurfural, acetic acid, formic acid, and levulinic acid and will have a pH or less than about 1.5 and preferably of about 0.5.

Preconditioning of the Hydrolyzate

The hydrolyzate raw material as received is a conglomerate of chemical substances. Many of such substances act as inhibitory agents or toxins to the yeast while many of such substances are unknown in identity and effect. It is possible that the presence of such substances, known or unknown, may exert a cumulative affect on the fermentation mechanism or yeast culture. It is also possible that some of the substances may be combining synergistically to inhibit either the particular yeast organism or other mechanism involved in the fermentation. Thus, while there is necessarily a degree of uncertainty as to exactly how the objectives of this invention are realized, it is believed that the preconditioning method renders the hydrolyzate fermentable either through removal of toxin substances or through conversion of at least a portion of such substances to non-toxin forms.

Several materials that are known toxins have been found to be present in the acid hydrolyzates derived from the lignocellulosic materials utilized herein. Their effect has been quantified to enable elimination or at least minimization of the same. The effect of such substances may be seen from the results of the following experiments in which an anaerobic culture of Saccharomyces uvarum was employed at about 0.7 dry weight percent cell concentration with acid hydrolyzates under the conditions indicated and employing identical inoculum and fermentation media. Glucose sugar determination was made using a Beckman Glucose Analyzer.

Where fermentation was achieved or attempted, the steam stripped, CaO pre-treated hydrolyzate was neutralized with HCl as the neutralizing agent.

Cell concentration as referred to herein is determined by optical density or dry weight measurements.

1. Acetic and Formic Acids

Both acids are toxins to the alcohol-producing yeast. Acetic acid is present in the hydrolyzate in concentrations of about 3 to 4 g/l while formic acid is present in amounts of about 8 to 9 g/l. The toxic effect of these acids can be negated by conducting the fermentation at a pH of about 5 to 7, preferably about 5.5 to 6.5. Fermenting below about pH 5 to 6 does not negate the effect of the toxins while fermenting above pH 7 is unfavorable for ethanol production. The parameters may best be illustrated by the results from the following experiments in which a newspaper hydrolyzate was preconditioned in accordance with the invention and analyzed for formic and acetic acids. A control solution of pure glucose was also provided. Identical nutrients in identical amounts were added to each of the solutions. Each of the solutions was inoculated with 0.7% yeast cells and allowed to ferment for 18 hours. The results were as indicated in Table I.

TABLE I

Fermentation of Glucose in Presence of Formic and Acetic Acids at pH 4.0 and pH 7.0

| | | g/l | |
|---|---|---|---|
| | | pH 4.0 | pH 7.0 |
| A. | Control Experiment | | |
| | Initial Glucose | 40.0 | 40.0 |
| | Added Formic Acid | 9.0 | 9.0 |
| | Added Acetic Acid | 4.0 | 4.0 |
| | Final Glucose | 41.0 | 0 |
| | Final Ethanol | 0 | 18.5 |
| | % Yield (based on Glucose) | 0 | 46.3% |
| B. | Newspaper Hydrolyzate | | |
| | Initial Glucose | 36.4 | 39.8 |
| | Contains Formic Acid | 3.0 | 3.0 |
| | Contains Acetic Acid | 3.0 | 3.0 |
| | Final Glucose | 36.4 | 0 |
| | Final Ethanol | 0 | 18.9 |
| | % Yield | 0 | 47.5% |

2. 5-Hydroxymethylfurfural (HMF)

HMF is a strong inhibitor of yeast growth. However, this material can be destroyed or degraded by CaO treatment at room temperature at a pH of about 10 to about 10.5 without adversely affecting the glucose. The pH range is believed to be critical herein since at a pH below about 10, the effect of HMF is not negated while at a pH above about 10.5, the sugar product is unstable. It has been discovered that CaO treatment of the hydrolyzates at pH 10 to 10.5 results in rapid depletion of HMF during the first two hours and levels off after that period. For example, it was observed that approximately 63% of the HMF is removed in 1 hour at pH 10.5. At pH 10.25, approximately 2 hours is required to remove the same amount of HMF while at pH 10.75, some glucose is concomitantly destroyed. Therefore, in the preferred embodiment of the invention, hydrolyzate is treated with sufficient CaO, at room temperature and with stirring, to maintain the pH at about 10.5 for about 1 to 1.5 hours.

The effect of the HMF on the yeast may be seen from the following experiments in which yeast growth as a function of HMF concentration in the hydrolyzate was determined at a pH within the fermentation range of 6 to 7. The doubling time is that time it takes for a cell to reproduce itself and was determined by optical density measurements.

| HMF, g/l | Doubling Time, hours | Growth Rate, h-' |
|---|---|---|
| 0 | 4.6 | 0.15 |
| 3 | 9.7 | 0.071 |
| 5 | 11.7 | 0.059 |
| 7 | 13.6 | 0.051 |

Growth Rate = $\frac{\ln 2}{\text{Doubling Time}}$

3. Levulinic Acid

Levulinic acid inhibits yeast growth at concentrations of 10 g/l or greater at pH 6-7.

| Levulinic Acid, g/l | Doubling Time, h. | Growth Rate, h-' |
|---|---|---|
| 0 | 4.6 | 0.150 |
| 10 | 7.0 | 0.099 |
| 20 | 20.4 | 0.034 |
| 30 | 18.7 | 0.37 |
| 40 | 22 | 0.32 |

No sequence in the preconditioning step is believed to negate the effect of this toxin material. Fermentations are obtained, it is believed, because of the removal or negation of the effect of other toxins present which may have a cummulative or synergistic effect with the levulinic acid. Additionally, as discussed further hereinbelow, levulinic-insensitive yeast also provide an alternative means for further negating the effect of this toxin.

4. Furfural

Furfural is toxic at concentrations in excess of 5.0 g/l. At concentrations between about 3 to 5 g/l, it has been found to markedly inhibit yeast growth.

| Furfural g/l | Doubling Time, hours (h) | Growth Rate, h-' |
|---|---|---|
| 0 | 4.6 | 0.150 |
| 2.0 | 4.2 | 0.165 |
| 4.0 | 7.4 | 0.094 |
| 5.0 | — | 0 |

Furfural is readily eliminated from the hydrolyzate either by steam-stripping or calcium oxide treatment or both.

The effect of steam-stripping and CaO pretreatment may be illustrated by the following experiments in which hydrolyzate at pH of about 6.8 was admixed with an anaerobic culture of Saccharomyces uvarum yeast at about 0.7% dry weight cell concentration in a shake flask and observed for fermentation of glucose after 16 hours. The results were as tabulated below in Table II.

TABLE II

| Treatment | Glucose g/l | Furfural g/l | HMF g/l | Glucose after 16 h growth g/l |
|---|---|---|---|---|
| A. Effect of Steam Stripping CaO Treated Hydrolyzate | | | | |
| A. None | 44 | 10.0 | 4.6 | 44 |
| B. CaO | 44 | 5.0 | 1.6 | 44 |
| C. Steam stripping of B | 44 | 1.2 | 2.2 | 0 |
| D. Adding furfural to C | 44 | 4.2 | 2.2 | 0 |
| B. Effect of CaO Treatment on Steam Stripped Hydrolyzate | | | | |
| A. None | 44 | 10 | 4.6 | 44 |
| B. Steam stripping | 42 | 1.2 | 4.4 | 42 |
| C. CaO treatment of B | 41 | 0.1 | 0.1 | 0 |

It will be seen from the above, that neither CaO treatment alone nor stripping with steam alone is effective to render the hydrolyzate fermentable although both treatments reduce the furfural content. It was found that addition of furfural to CaO treated and steam-stripped hydrolyzate to a concentration nearly equal to that after CaO treatment but before steam-stripping did not inhibit the growth. This indicated that the steam-stripping may be removing some additional unknown inhibiting material.

It will be seen from the above that the steps of (1) steam-stripping; (2) treating with CaO at a pH of 10 to 10.5; and (3) fermentation at pH 5 to 7 are critical to the successful operation of the preconditioning stage of the process.

Various additional steps may be interjected between the essential steps of the preconditioning method, if desired. Thus, in the preferred mode of the invention, the hydrolyzate having a pH of about 0.5 is partially neutralized with limestone or ammonium hydroxide to a pH of about 4 prior to steam-stripping. While the hydrolyzate may be steam-stripped either at low pH as received or at pH 4 after partial neutralization, partial neutralization prior to steam-stripping is desirable to reduce corrosion of equipment. This step necessitates an additional filtration step to remove precipitated material and may be omitted in the event equipment is employed that is not readily corroded or whenever corrosion is not a significant concern. Where the hydrolyzate is neutralized to pH 4 employing calcium carbonate, etc., the resultant precipitate may be incinerated after recovery from the hydrolyzate to provide the fuel for generation of the steam for the process. Normally, prior to incineration, the filter cake will be washed to remove and recover sugars, with the washings being added to the hydrolyzate filtrate.

Neutralizing the hydrolyzate with ammonium hydroxide has the added advantage of supplying a nutrient which the fermentation microorganism can use for its growth while at the same time raising the pH of the hydrolyzate to prevent corrosion.

Steam-stripping is accomplished preferably by injecting steam into the hydrolyzate in an amount sufficient to maintain the hydrolyzate at a temperature of about 95° to 105° C. Conveniently, the hydrolyzate may be passed through a countercurrent extractor to remove steam-volatiles. In this technique, steam is introduced at the bottom of the column and the hydrolyzate is introduced at the top and collected in a vessel at the bottom of the column. Steam-volatile toxins are removed in the steam which is condensed and collected in a separate vessel.

After steam-stripping, the hydrolyzate is treated with sufficient CaO to maintain the pH between about 10 and 10.5 for a period of about 1 to 3 hours at room temperature after which the precipitate is removed by any convenient means including filtration, centrifugation, etc.

The hydrolyzate, after neutralization with a mineral acid and removal of the resultant precipitate, is fermentable at this stage, the rapidity of the reaction having been found to be dependent on the concentration of the sugar solution, the particular yeast strain employed, the yeast cell concentration and the mineral acid used to neutralize the conditioned hydrolyzate.

Effect of Mineral Acid

The hydrolyzate is neutralized to a pH of about 5 to 7, and preferably 5.5 to 6.5 after CaO treatment employing a mineral acid, e.g. hydrochloric acid, sulfuric acid, phosphoric acid, etc. Phosphoric acid is especially preferred for several reasons. Neutralizing with hydrochloric or sulfuric acid results in a turbid solution which is of no consequence in batch fermentation. However, in a continuous culture fermentation, yeast cells must be recycled from the effluent stream back to the fermentor and must be reconcentrated prior to such recycling. The use of phosphoric acid as the neutralizing acid results in clarification of the hydrolyzate and thereby enhances reconcentration and recycling of the yeast cells. Even more significantly, as discussed further hereinbelow, it has been discovered that the use of phosphoric acid results in more rapid fermentation and when employed in combination with a high concentration of yeast cells, results in extremely rapid fermentation rates with concentrated hydrolyzates making it possible to realize theoretical yields after fermentation for as short a period as 1 to 3 hours.

Effect of Concentration of Hydrolyzate

It was discovered that preconditioning of the hydrolyzate by CaO pretreatment, steam-stripping and addition of mineral acid, e.g. HCl neutralization to pH 6 to 7, lead to fermentable solutions that became progressively more difficult to ferment as the glucose concentration was increased over 50 g/l. It appears that concentration of the solution also increases the level of other inhibitory substances in the hydrolyzate beyond the tolerable level. To counteract this inhibition of concentrated solutions, different yeast and yeast concentrations were evaluated as discussed further hereinbelow. However, to illustrate the effect of the concentration step, typical results obtained with anaerobically propagated *Candida utilis* at a cell concentration of 0.7% with sawdust hydrolyzate neutralized with HCl and fermented for about 16 hours may be seen from results of the following experiments.

| Treatment | Glucose g/l | Glucose after Growth g/l |
|---|---|---|
| A. None | 44.0 | 44.0 |
| B. CaO and stripping | 44.0 | 0 |
| C. Concentrating B | 100.0 | 100.0 |
| D. Diluting C to | 70.0 | 49.5 |
| E. Diluting C to | 60.0 | 0 |
| F. Diluting C to | 50.0 | 0 |

Attempts to ferment hydrolyzate solutions concentrated to 150 g/l or greater have not been successful even when employing the means discussed below.

Effect of Yeast Strain, Cell Concentration and Neutralizing Acid

The above-results were obtained in shake flasks using either *Candida utilis* or *S. uvarum* as the yeast culture and HCl as the neutralizing acid.

Other yeast strains were tested and evaluated for effect on the fermentability of the preconditioned hydrolyzate when neutralized with HCl.

*S. uvarum* at 0.7% cells at dry weight was observed to ferment 100 g/l hydrolyzate in about 50 g/l hydrolyzate solutions in about 19 hours while *S. cerevisiae* (Baker's yeast) fermented 100 g/l hydrolyzate in about 98 hours and 42 hours to a 50.8 g/l ethanol concentration. A levulinic acid-insensitive strain of *S. uvarum* was produced and isolated by exposure of the cells to levulinic acid in chemostat culture. This strain at 0.7% concentration was found to ferment 100 g/l hydrolyzate in about 50 hours resulting in 49.3 g/l ethanol.

It was then discovered that use of phosphoric acid as the neutralizing acid had a definite positive effect on the rate of fermentation of the concentrated hydrolyzates. Thus, phosphoric acid treated hydrolyzates at 100 g/l, when fermented with either the parent strain *S. uvarum* or with the levulinic acid-insensitive strain of *S. uvarum*, both at 0.7% cell concentration, resulted in yields of 47.7 g/l ethanol in 15.5 hours while Baker's yeast at the same concentration resulted in 46.5 g/l ethanol in 11.5 hours.

Even more rapid fermentation to theoretical yield is possible when using higher yeast cell concentrations as will be illustrated by the results obtained and listed below in Table III.

TABLE III

Effect of Cell Concentration on 100g/l Phosphoric Acid-Neutralized Sawdust Hydrolyzate-Baker's Yeast

| Cell Dry-Weight % | Time Required Hours | Ethanol Yield, % |
|---|---|---|
| 0.7 | 20 | 50. |
| 1.5 | 12 | 48.1 |
| 2.0 | 8 | 50.6 |
| 2.5 | 5.6 | 50.2 |
| 3.0 | 3.0 | 46.8 |
| 5.0 | 1.5 | 47.8 |
| 7.0 | 1.25 | 48.4 |

The interrelationship and interdependence of the various steps of the preconditioning stage of the process as well as the effect of the particular neutralizing acid and yeast cell concentration may be readily appreciated from a consideration of the above experiments.

The function of the CaO treatment to effectively remove or degrade HMF in periods as short as 1 to 3 hours, the effect of neutralizing to pH 5 to 7, the effect of the concentration of the hydrolyzate and yeast cells and the achievement of extremely rapid reaction rates of concentrated hydrolyzates when neutralized with phosphoric acid are each significant factors that are unexpected and appear to serve a vital function in the context of the overall process.

Provision of Fermentation Medium

Following the preconditioning method, the hydrolyzate is ready for fermentation by either a batch or continuous culture fermentation process under aerobic or anaerobic cell propagation conditions.

Inoculum of the various yeast strains may be developed by any method well known in the art. Any yeast may be employed that is capable of growth in the fermentation medium. As discussed above, satisfactory results have been obtained with members of the genus Saccharomyces, such as *S. uvarum, S. uvarum* modified to be levulinic-insensitive, *S. cerevisiae* (Baker's yeast), etc. with Baker's yeast being especially preferred. Satisfactory results have also been obtained with *C. utilis* at glucose concentrations up to about 60 g/l. This particular yeast has not been found to be effective at higher glucose concentrations.

Suitable microbial growth nutrients may be added to the hydrolyzate and to the inoculum development medium as desired including phosphorous and nitrogen in the form of phosphate, ammonium, urea, etc. When phosphoric acid is the neutralizing acid, phosphorous nutrient is added during the neutralization step. Additionally, when phosphoric acid is employed as the neutralizing acid, fermentation may be realized by addition of urea as the sole additive nutrient source. Partial neutralization with ammonium hydroxide prior to steam stripping also adds nitrogen as a nutrient source. Other mineral salts, trace elements, vitamins, etc. including ammonium sulfate, magnesium sulfate, sodium chloride, calcium chloride, potassium phosphate, biotin, folic acid, inositol, niacin, p-aminobenzoic acid, riboflavin, thiamine, urea, etc. may be added to the hydrolyzate as growth nutrients, as desired.

In a preferred embodiment, inoculum for batch fermentation is developed by inoculating a loopful of cells from a slant on a medium containing about 2.0% glucose, 1.0% peptone, and 0.3% yeast extract (hereafter referred to as YPG medium). Medium thus inoculated is incubated with shaking for 24 hours at 32° C. after which it is transferred into 900 millimeters of additional YPG medium, incubated with shaking for 6 to 8 hours and transferred to a fermentor containing 9 liters of ID medium comprising 90 g/l glucose, 7.65 g/l yeast extract, 1.19 g/l ammonium chloride, 0.01 g/l magnesium sulfate, 0.05 g/l calcium chloride, and 0.2 mls./l of GE 60 AF, an antifoam agent (available from general Electric Co.). Cells are aerobically propagated at pH 6–7 under 1,000 rpm agitation and 1 vvm air flow for 16 to 20 hours after which the cells may be recovered by centrifugation or equivalent means and employed in the desired concentration to inoculate the hydrolyzate.

Cells may also be developed from a continuous culture whereby cells are separated from ethanol product removed from the fermentor. In this step, recovered cells are reconcentrated and recycled under conditions that preserve the metabolic state of the cell, the volume in the fermentor and the constant value of the cell concentration in the fermentor. Cell separation from the ethanol product may be accomplished by various means including gravity settling, centrifugation, ultrafiltration, etc. Preferably, the cells are recovered and recycled through the use of dual output streams emanating from the fermentor. For example, ethanol and yeast cells are metered out in a first output stream at a rate determined by a sensor in the fermentor which determines when the cell concentration has exceeded a desired upper limit. A second output stream removes ethanol and yeast cells to a cell recycler comprising a suitable membrane, for example a microporous filter as employed in ultrafiltration, which retains the cells but allows the ethanol and unmetabolized medium to penetrate permitting recovery of substantially cell-free ethanol. The membrane permits continuous cell concentration from which cells may be recycled to the fermentor as needed as fresh preconditioned hydrolyzate streams are fed for fermentation.

The following illustration will serve to illustrate a batch fermentation in accordance with the invention.

Illustration of a Preferred Embodiment

Acid hydrolyzate having a pH of about 0.5 was produced from sawdust by acid hydrolysis in the presence of steam and sulfuric acid in a reaction zone maintained at a temperature of about 190° to 225° C. under pressure of about 200 to 400 psi. The hydrolyzate contained about 50.2 g/l glucose, 8.9 g/l furfural, 3.6 g/l 5-hydroxymethylfurfural, 6.5 g/l levulinic acid, 9.7 g/l acetic acid and 4.8 g/l formic acid.

The hydrolyzate was partially neutralized with sufficient ammonium hydroxide to a pH of about 4 after which the resultant precipitate was removed and the partially neutralized stream fed to a countercurrent extractor where it was subjected to steam at a rate of 4 l/h during which steam volatile materials including furfural were removed and collected. 14 g/l of CaO was added to the steam-stripped hydrolyzate material to adjust the pH to about 10.5, the mixture was stirred at room temperature and maintained at pH 10.5 for about 1 hour after which the resultant precipitate was removed. The hydrolyzate was neutralized to pH 5.5 to 6.5 with 1.5–3.0 ml/l of phosphoric acid and the resultant precipitate was removed. The neutralized hydrolyzate was then concentrated to a glucose concentration of about 100 g/l by heating at 35° C. under vacuum of 28 inches Hg using a continuous evaporator.

After cooling to room temperature, 0.1% urea was added to the concentrated hydrolyzate which was next fed to the fermentor together with a sufficient amount of preformed inoculum comprising Baker's yeast aerobically propagated on an agar slant in YPG medium to give a dry cell concentration of about 3 to 3.5 weight percent.

The mixture was anaerobically fermented for about 1.5 to 2 hours after which about 50 g/l of ethanol was recovered.

Yeast cells were recovered by centrifugation and transferred to a subsequent fermentation batch. Satisfactory results were obtained for several transfers.

It will be apparent to those skilled in the art that various changes may be made without departing from the spirit and scope of the invention and that the invention is not limited to the preferred embodiments that have been described and illustrated hereinabove.

We claim:

1. A method for preconditioning acid hydrolyzates derived from lignocellulosic materials comprising glucose and substances which tend to inhibit the fermentation thereof, consisting essentially of the steps of:
   (1) subjecting said acid hydrolyzate to steam to remove steam-volatile substances therefrom;
   (2) adding sufficient calcium oxide to said steam-stripped hydrolyzate to adjust the pH to between 10 and about 10.5 and maintaining said mixture at said pH for about 1 to 3 hours;
   (3) adding sufficient amounts of a mineral acid to adjust the pH of said hydrolyzate to about 5 to 7; and (4) adjusting the concentration of said hydrolyzate to a glucose concentration of less than 150 grams per liter to provide a solution fermentable to ethyl alcohol, with the proviso that when said concentration is greater than 50 grams per liter, the mineral acid employed in step (3) is phosphoric acid.

2. A method for preconditioning acid hydrolyzates as claimed in claim 1 wherein said acid hydrolyzate provided in step (1) has a pH within the range of 0.5 to 1.5 and is derived from sawdust or newspaper.

3. A method for preconditioning acid hydrolyzate as claimed in claim 2 wherein prior to subjecting the hydrolyzate to steam, the hydrolyzate is partially neutralized to a pH of about 4 with a sufficient amount of calcium carbonate or ammonium hydroxide and the resulting precipitate is separated therefrom.

4. A method for preconditioning acid hydrolyzates as claimed in claim 3 wherein the mineral acid employed in step (3) is phosphoric acid.

5. A method of preconditioning acid hydrolyzates as claimed in claim 1 wherein said hydrolyzate is concentrated in step (4) to a glucose concentration of at least 100 grams per liter but less than 150 grams per liter.

6. A method for preconditioning acid hydrolyzates as claimed in claim 5 wherein acid hydrolyzate is concentrated by heating to about 35° C. under a vacuum of about 28 to 30 inches Hg.

7. A method for preconditioning acid hydrolyzates derived from lignocellulosic materials to negate the effect of substances tending to inhibit the fermentation thereof, consisting essentially of the steps of:
(1) providing an acid hydrolyzate comprising glucose, furfural, 5-hydroxymethylfurfural, acetic acid and formic acid having a pH of about 0.5 to 1.5;
(2) partially neutralizing said hydrolyzate to a pH of about 4 with a sufficient amount of ammonium hydroxide;
(3) subjecting the partially neutralized hydrolyzate to steam to remove a major proportion of furfural and other steam-volatile substances therefrom;
(4) adding sufficient calcium oxide to the steam-stripped hydrolyzate to adjust the pH to about 10.5 and maintaining said pH at room temperature for about 1 hour to degrade 5-hydroxymethylfurfural;
(5) adjusting the pH of the hydrolyzate to about 5 to 7 with a sufficient amount of phosphoric acid and separating said hydrolyzate from the precipitate thus produced; and
(6) concentrating the hydrolyzate to a glucose concentration of at least about 100 grams per liter but less than 150 grams per liter under conditions that minimize degradation of the glucose to provide a solution fermentable to ethyl alcohol.

8. A process for preconditioning acid hydrolyzate as claimed in claim 7 wherein said hydrolyzate is derived from sawdust or newspaper.

9. A process for preconditioning acid hydrolyzates as claimed in claim 7 wherein said hydrolyzate is concentrated in step (6) by heating to a temperature of about 35° C. under a vacuum of about 28 to 30 inches hg.

10. A process for the production of ethyl alcohol from glucose contained in an acid hydrolyzate derived from lignocellulosic materials, comprising the steps of:
(1) preconditioning said acid hydrolyzate to negate the effect of substances tending to inhibit the fermentation thereof by subjecting said hydrolyzate to the method of claim 1;
(2) inoculating the preconditioned hydrolyzate with yeast inoculum developed from a strain that is capable of growth in the hydrolyzate fermentation medium;
(3) permitting said inoculated hydrolyzate to ferment at a pH of about 5 to 7 for a period sufficient to convert glucose to ethyl alcohol; and
(4) recovering ethyl alcohol from the fermentation medium.

11. A process for the production of ethyl alcohol as claimed in claim 10 wherein said yeast is Baker's yeast.

12. A process for the production of ethyl alcohol as claimed in claim 11 wherein yeast cells are recovered from the fermentation mixture and recycled to a subsequent fermentation medium.

13. A process for the production of ethyl alcohol from glucose contained in an acid hydrolyzate derived from lignocellulosic materials, comprising the steps of:
(1) providing an acid hydrolyzate comprising glucose, furfural and 5-hydroxymethylfurfural and having a pH of about 0.5 to 1.5;
(2) preconditioning said hydrolyzate to negate the effect of substances tending to inhibit the fermentation thereof by subjecting said hydrolyzate to the method of claim 4;
(3) inoculating the preconditioned hydrolyzate with yeast inoculum developed from a strain that is capable of growth in the hydrolyzate fermentation medium;
(4) permitting said inoculated hydrolyzate to ferment at a pH of 5.5 to 7 for a period sufficient to convert glucose to ethyl alcohol; and
(5) recovering ethyl alcohol from the fermentation medium.

14. A process for the production of ethyl alcohol from glucose contained in an acid hydrolyzate derived from lignocellulosic materials, comprising the steps of:
(1) providing an acid hydrolyzate comprising glucose, furfural and 5-hydroxymethylfurfural;
(2) preconditioning said hydrolyzate to negate the effect of substances tending to inhibit the fermentation thereof by subjecting said hydrolyzate to the steps of (a) steam-stripping furfural and other steam volatile substances therefrom; (b) adding sufficient calcium oxide to said steam-stripping hydrolyzate, at room temperature to adjust the pH to about 10.5 and maintaining said solution at said pH for a period of about 1 hour and separating the resulting precipitate from said hydrolyzate; (c) adjusting the pH of said hydrolyzate to about 5 to 7 with phosphoric acid and separating the resultant precipitate; and (d) adjusting the concentration of the neutralized hydrolyzate to a glucose concentration of at least about 100 grams per liter but less than 150 grams per liter;
(3) inoculating said preconditioned hydrolyzate with Baker's yeast inoculum comprising from about 0.7 to about 7 dry weight percent of yeast cells per 100 grams per liter of glucose in said hydrolyzate;
(4) fermenting said inoculated hydrolyzate at a pH of 5 to 7 for 20 to 1.5 hours to convert glucose to substantially quantitative amounts of ethyl alcohol; and
(5) recovering ethyl alcohol from the fermentation mixture.

15. A process for the production of ethyl alcohol as claimed in claim 14 wherein said hydrolyzate is derived from newspaper or sawdust.

16. A process for production of ethyl alcohol as claimed in claim 14 wherein said hydrolyzate is adjusted to a pH of about 4 with ammonium hydroxide prior to said preconditioning step.

17. A process for the production of ethyl alcohol as claimed in claim 14 wherein urea is added to said hydrolyzate prior to said inoculation step.

18. A process for the production of ethyl alcohol as claimed in claim 14 wherein the inoculum added in step (3) comprises from about 3 to 3.5 dry weight percent of yeast cells per 100 grams per liter of glucose in said hydrolyzate.

19. A process for the production of ethyl alcohol as claimed in claim 18 wherein said fermentation is complete in about 2 to 3 hours.

20. A process for the production of ethyl alcohol from glucose contained in an acid hydrolyzate derived from a lignocellulosic material which comprises the steps of:
(1) introducing into a fermentor an acid hydrolyzate that has been preconditioned to negate the effect of substances tending to inhibit the fermentation thereof by the method of claim 1, said fermentor containing a performed yeast culture capable of growth in said hydrolyzate medium;
(2) substantially continuously maintaining said yeast culture in said fermentor at a concentration of about 0.7 to about 7 dry weight percent cells per 100 grams per liter of glucose in said fermentor;
(3) permitting said hydrolyzate to ferment at a pH of 5 to 7 for a period sufficient to convert glucose to ethyl alcohol;
(4) removing an ethyl alcohol stream from the fermentor;
(5) separating yeast cells from said ethyl alcohol stream; and
(6) reconcentrating said yeast cells and recycling the concentrated cells to said yeast culture maintained in said fermentor.

21. A method for preconditioning acid hydrolyzate as claimed in claim 1 wherein said hydrolyzate is separated from precipitate formed in step (2).

22. A method for preconditioning acid hydrolyzates as claimed in claim 1 wherein said hydrolyzate is separated from precipitate formed in step (3).

23. A method for preconditioning acid hydrolyzates as claimed in claim 1 wherein said hydrolyzate is separated from precipitate formed in steps (2) and (3).

24. A method for preconditioning acid hydrolyzates derived from lignocellulosic materials comprising glucose and substances which tend to inhibit the fermentation thereof, consisting essentially of the steps of:
(1) providing said acid hydrolyzate having a pH of about 0.5 to 1.5;
(2) subjecting said acid hydrolyzate to steam to remove steam-volatile substances therefrom;
(3) partially neutralizing said hydrolyzate to a pH of about 4 with a sufficient amount of calcium carbonate;
(4) adding sufficient calcium oxide to said steam stripped hydrolyzate to adjust the pH to about 10.5 and maintaining said mixture at said pH for about 1 to 3 hours;
(5) adjusting the pH of the hydrolyzate to about 5 to 7 with a sufficient amount of phosphoric acid and separating said hydrolyzate from the precipitate thus produced; and
(6) concentrating the hydrolyzate to a glucose concentration of at least about 100 grams per liter but less than 150 grams per liter under conditions that minimize degradation of the glucose to provide a solution fermentable to ethyl alcohol.

25. A fermentable solution produced in accordance with the method of claim 1.

26. A fermentable solution produced in accordance with the method of claim 7.

27. A fermentable solution produced in accordance with the method of claim 24.

* * * * *